United States Patent [19]

Messina

[11] Patent Number: 4,543,351

[45] Date of Patent: Sep. 24, 1985

[54] SPIRONOLACTONE CONTAINING COMPOSITION FOR COMBATTING ACNE

[75] Inventor: Michele Messina, Turin, Italy

[73] Assignee: Schiapparelli Farmaceutici S.p.A., Turin, Italy

[21] Appl. No.: 593,926

[22] Filed: Mar. 27, 1984

[30] Foreign Application Priority Data

Apr. 1, 1983 [IT] Italy ................................ 20435 A/83

[51] Int. Cl.$^4$ .............................................. A61K 31/58
[52] U.S. Cl. .................................................... 514/175
[58] Field of Search ........................................ 424/241

[56] References Cited

U.S. PATENT DOCUMENTS 4,177,267 12/1979 Herschler ............................ 424/241
4,347,245 8/1982 Shapiro ............................... 424/241

Primary Examiner—Elbert L. Roberts
Attorney, Agent, or Firm—Oblon, Fisher, Spivak, McClelland & Maier

[57] ABSTRACT

A spironolactone containing composition for topical use in the form of a cream active in combatting acne and causing only skin absorption and therefore devoid of any undesired systemic effect.

3 Claims, No Drawings

SPIRONOLACTONE CONTAINING COMPOSITION FOR COMBATTING ACNE

BACKGROUND OF THE INVENTION

1. Field of the Invention

The present invention relates to a spironolactone composition for combatting acne.

2. Description of the Prior Art

Acne is a chronic phlogistic disease which is potentially present in all young people. It is clinically characterized by comedones, papules, nodules and cysts. No differences between sexes are noted and all human races are subjected to it.

Acne is considered as a physiological condition in adolescents. On the other hand it may be induced or aggravated by drugs, chemical agents such as oils, chlorinated hydrocarbons, tar and the like, and by conditions preventing perspiration such as too heavy clothes in tropical climates. Drugs favoring acne in predisposed subjects are ACTH, corticosteroids, testosterone, gonadotropins, oral contraceptives, trimethadone, iodides and bromides. Sometimes whole families are particularly hit by acne, and this fact suggest a hereditary factor. Dietetic factors were overevaluated in the past.

Lesions caused by acne are generally subdivided into phlogistic and non-phlogistic lesions. They are typically spread on the face, although periorbital areas are excluded, on the back, thorax and shoulders. Non-phlogistic lesions include open and closed comedones ("black spots" and "white spots"). An open comedo consists of a small flat or prominent area with a central hole containing keratine and lipids; actually, the comedo is a pilo-sebaceous follicle containing a keratine plug. The plug top is dark being oxidated. A closed comedonic pore is surmonted by epithelium; this is the lesion present as a papule unless the epithelium is removed. Since keratine is enclosed within the comedo, it represents a potential source of phlogistic lesions such as erythematous papules, nodules and cysts.

It has been now discovered that acne can be effectively combatted by percutaneous treatment with a spironolactone containing pharmaceutical composition. Spironolactone is generally used in those diseases in which its effectiveness may be attributed to its activity as an aldosterone antagonist. However, spironolactone generally displays a number of undesirable side effects due to a suggested interference with androgenic action, including decreased testosterone formation and other possible mechanisms, which may induce sexual impotence, decrease in libido, gynecomastia and similar disturbances of hormone balance.

It is therefore one purpose of this invention to provide a spironolactone composition effective in combatting acne, and at the same time being devoid of undesirable side effects, which may have a severe psychological influence on treated subjects, especially those who are in their age of growth and adolescence.

Another purpose of this invention is to provide such a spironolactone composition in the form of a cream, which on topical skin application gives an effective concentration of spironolactone on the site where it is desired it to act on acne with beneficial effects.

A further purpose of this invention is to provide such a spironolactone formulation which is only adsorbed by skin where it is applied, but does not penetrate through the skin in such a way as to be circulated in the body, thus preventing the above mentioned undesired side effects.

BRIEF SUMMARY OF THE INVENTION

The present invention relates to a spironolactone containing composition effective in combatting acne, capable to be locally absorbed by skin but not being absorbed by the deep tissues of the body, thus preventing systemic side effects of spironolactone. The composition is in form of a cream and contains a useful amount of spironolactone, a higher saturated fatty acid ester of ethylene glycol and of polyoxyethylene glycols, a saturated polyoxyethylene glycol glyceride and a substantial amount of water.

DETAILED DESCRIPTION OF THE INVENTION

The present invention relates to a spironolactone containing composition in the form of a cream, to be applied to human skin in areas affected by acne in order to effectively treat said disease.

By applying to the skin affected by acne the cream forming the object of the present invention, an effective control of the disease is obtained, while eliminating side effects usually connected with the use of spironolactone.

The spironolactone containing cream of this invention comprises an effective amount of spironolactone and a suitable carrier.

The amount of spironolactone in the cream may vary within a wide range, for instance in an amount ranging between 0.1 and 10 weight percent based on the total weight of the cream. Preferably, this amount ranges between 2.0 and 10 weight percent, and most preferably, between 5 and 10 percent. Quantities lower than 0.1 percent have a low degree of effectiveness, while quantities higher than 10 percent represent a non necessary concentration which does not help in getting improved results.

The carrier in which the active ingredient spironolactone is incorporated is a mixture of (1) a mixed polyethylene glycol and polyoxyethylene glycol ester of a higher saturated fatty acid, (2) a saturated polyoxyethylene glycol glyceride and (3) a substantial amount of water. Liquid paraffin may also be added to the carrier in an amount sufficient to keep the composition in a semi-fluid condition particularly fit for forming a final cream having the desired physical properties allowing a uniform distribution of the active ingredient on the site of application.

The mixed polyethylene glycol and polyoxyethylene glycol ester of a higher saturated fatty acid is an ester of a mixture of polyethylene glycol and polyoxyethylene glycols with a higher saturated fatty acid having at least 15 carbon atoms, such as palmitic, stearic, palmitoyl stearic, stearoypalmitic acid and the like. These ingredients, which, in general, are commercially available products, may be present in the cream in an amount ranging from 10 and 25 weight percent based on the weight of the cream, but preferably between 15 and 20 weight parts.

The saturated polyoxyethylene glycol glyceride is the mono-, di- and/or triglyceride of a polyoxyethylene glycol. Also these ingredients are commercially available products and may be present in the cream in an amount ranging between 2 and 10 weight percent based on the weight of the cream, but preferably between 3 and 5 percent.

Water is an essential component of the cream, being present in an amount ranging between 60 and 75 weight percent based on the total weight of the cream. Preferably, the amount of water ranges between 65 and 75 percent, most preferably between 70 and 75 percent.

Usual preservatives are conveniently added to the composition, such and in such quantities as is taught by the art. For instance, methyl, ethyl, propyl and/or butyl p-hydroxy-benzoate may be present in the currently used small amounts, normally not higher than 0.2–0.5 weight percent based on the total weight of the cream.

Liquid paraffin may also be added to the cream composition of the invention, in an amount ranging from 1 to 5 weight percent based on the total weight of the cream.

Of course, all non-active ingredients of the spironolactone composition of this invention are present in such a mutual ratio as to give the cream the most acceptable degree of consistence and fluidity necessary or simply useful to obtain the herein claimed results.

The application dosage of the cream may vary depending on the severity of acne and the spironolactone concentration in the cream. The dosage is usually controlled in such a way as to apply daily from about 10 to about 250 mg of spironolactone on the face skin, and from about 25 to about 1000 mg of spironolactone on the back, i.e. on the two more frequently affected areas of the skin. These daily dosages may be applied on the skin once a day, ore preferably subdivided into several lower dosages at 4–12 hours intervals, so as to insure a regular absorption by the skin of the active ingredient.

EXAMPLES 1 TO 5

A cream for topical use on the skin may be prepared from the following ingredients and in the given percentages in weight (grammes).

| Ingredient | Formulation | | | | |
|---|---|---|---|---|---|
| | A | B | C | D | E |
| Spironolactone | 2.0 | 5.0 | 10.0 | 2.0 | 5.0 |
| Polyethylene glycol and polyoxyethylene glycol palmitostearate (1) | 18.0 | 16.5 | 15.5 | 18.0 | 16.5 |
| Saturated polyoxyethylenated glycerides (2) | 5.0 | 4.0 | 4.0 | 5.0 | 4.0 |
| Liquid paraffin | 4.5 | 4.0 | 3.5 | 2.5 | 2.0 |
| Lavanda essence | — | — | — | 2.0 | 2.0 |
| Methyl p-hydroxybenzoate | 0.12 | 0.1 | 0.12 | 0.12 | 0.12 |
| Propyl p-hydroxybenzoate | 0.05 | 0.05 | 0.05 | 0.05 | 0.05 |
| Sodium methyl p-hydroxybenzoate | 0.03 | 0.05 | 0.03 | 0.03 | 0.03 |
| Water | 70.3 | 70.3 | 66.8 | 70.3 | 70.3 |

(1) TEFOSE 63 supplied by Etablissements Gattefosse. Saint Priest Cedex. France
(2) LABRAFIL 2130 CS supplied by Gattefosse.

EXAMPLE 6

Sixty-five patients of an age comprised between 15 and 25 years, of which 30 women and 35 men, suffering on the face and/or the back for acne of 2nd, 3rd or 4th degree of the Pillsburg et al. classification, A Manual of Cutaneous Medicine, W. B. Saunders Co. Philadelphia, Pa. 1961, pages 273–276, were treated with the 5 percent spironolactone cream (Example 1-5, cream E) in such an amount to have a daily administration of about 75 mg of active substance on the face and about 130 mg of active substance on the back subdivided into two daily applications. Treatment was continued for 40 days.

Observation of the patients was made by the same observer before treatment and 20 and 40 days after administration. Pictures were taken on the involved skin areas before starting treatment and at the 20th and 40th day of treatment.

The clinical response was highly positive in 36 patients within 20 days; in 12 of these patients the acne lesions totally disappeared after 40 days of treatment. Other 24 patients showed clinical improvement after only 40 days. In only 5 patients no perceptible improvement occurred.

Five patients showed facial erythema and sensation of burning after application of the cream. These symptoms disappeared spontaneously even when treatment was not suspended. In no case undesirable systemic side effects were noted, such as are usually noted by oral spironolactone administration.

Serum and urine samples were taken from all patients at several time intervals. No traces of spironolactone or products attributable to metabolic conversion of the same were detected at any time by a high pressure liquid chromatography technique with extremely high sensitivity.

The obtained results show that percutaneous spironolactone treatment with the cream composition of this invention is highly useful in combatting acne while preventing the severe side effects usually occurring after systemic spironolactone treatment.

I claim:
1. A topical composition comprising:
   A. from 0.1 to 10 weight percent of spironolactone as the active ingredient;
   B. from 10 to 25 weight percent of a mixed polyethylene glycol and polyoxyethylene glycol ester of a higher saturated fatty acid;
   C. from 2 to 10 weight percent of a saturated polyoxyethylene glycol glyceride; and
   D. from 60 to 75 weight percent of water.
2. The composition of claim 1, further containing a preservative selected from methyl p-hydroxybenzoate, propyl p-hydroxybenzoate, sodium methyl p-hydroxybenzoate and their mixtures.
3. A method of treating acne comprising topically applying a composition comprising
   A. from 0.1 to 10 weight percent of spironolactone as the active ingredient;
   B. from 10 to 25 weight percent of a mixed polyethylene glycol and polyoxyethylene glycol ester of a higher saturated fatty acid;
   C. from 2 to 10 weight percent of a saturated polyoxyethylene glycol glyceride; and
   D. from 60 to 75 weight percent of water from claim 1, to a person in need of such treatment.

* * * * *